US005877321A

United States Patent [19]

Emonds-Alt et al.

[11] Patent Number: 5,877,321
[45] Date of Patent: Mar. 2, 1999

[54] DIALKYLENEPIPERIDINO COMPOUNDS AND THEIR ENANTIOMERS, PROCESS FOR PREPARING THEM AND PHARMACEUTICAL COMPOSITIONS CONTAINING THEM

[75] Inventors: Xavier Emonds-Alt, Combaillaux; Isabelle Grossriether, Uzes; Vincenzo Proietto, St Georges D'Orques; Didier Van Broeck, Murviel Les Montpellier, all of France

[73] Assignee: Sanofi, Paris, France

[21] Appl. No.: 452,372

[22] Filed: May 26, 1995

Related U.S. Application Data

[62] Division of Ser. No. 191,085, Feb. 4, 1994, Pat. No. 5,446,052, which is a division of Ser. No. 877,779, May 4, 1992, Pat. No. 5,300,648.

[30] Foreign Application Priority Data

May 3, 1991 [FR] France .................................. 91 05489

[51] Int. Cl.$^6$ .................................................. C07D 211/06
[52] U.S. Cl. .......................... 546/226; 546/193; 546/201; 546/202; 546/229; 546/236
[58] Field of Search ...................................... 546/226, 236, 546/193, 201, 202, 229

[56] References Cited

U.S. PATENT DOCUMENTS

| | | | |
|---|---|---|---|
| 3,528,984 | 9/1970 | Cavalla et al. ........................... | 546/230 |
| 4,310,532 | 1/1982 | Roll ........................................... | 514/331 |
| 4,481,207 | 11/1984 | Manoury et al. ........................ | 514/331 |
| 4,604,393 | 8/1986 | Cornu et al. ............................. | 514/229 |
| 4,962,113 | 10/1990 | Trushima ................................. | 514/307 |
| 5,169,856 | 12/1992 | Gute et al. ............................... | 514/331 |

FOREIGN PATENT DOCUMENTS

| | | | |
|---|---|---|---|
| 0 330 026 | 8/1989 | European Pat. Off. . | |
| 1 211 691 | 3/1960 | France . | |
| 2 528 835 | 12/1983 | France . | |
| 2 531 702 | 2/1984 | France ................................... | 546/230 |
| 2676226 | 4/1991 | France . | |

OTHER PUBLICATIONS

Gotto et al., "The role of receptors in biology and medicine", Raven Press, p. 191, 1987.

*Primary Examiner*—Ceila Chang
*Attorney, Agent, or Firm*—Foley & Lardner

[57] ABSTRACT

A compound of formula XXII $$Q'-N\underset{}{\bigcirc}-(CH_2)_2-CH(Ar')-CH_2-Q''$$
(XXII)

wherein Ar', Q' and Q" are as defined in the specification are useful intermediates for making neurokinin receptor active compounds.

2 Claims, No Drawings

DIALKYLENEPIPERIDINO COMPOUNDS AND THEIR ENANTIOMERS, PROCESS FOR PREPARING THEM AND PHARMACEUTICAL COMPOSITIONS CONTAINING THEM

This application is a continuation, division, of application Ser. No. 08/191,085, filed Feb. 4, 1994 now U.S. Pat. No. 5,446,052 which is a division of application Ser. No. 07/877.779, filed May 4, 1992 now U.S. Pat. No. 5,300,648.

The present invention relates to new aromatic derivatives substituted with an amino group and with various ester, amine or amide functions, and to their enantiomers.

The present invention also relates to the process for obtaining the compounds, which may be enantioselective, and to the use of the compounds according to the invention in compositions for therapeutic application, and more especially in pathological phenomena involving the neurokinin system such as: pain (D. REGOLI et al., Life Sciences, 1987, 40, 109–117), allergy and inflammation (J. E. MORLAY et al., Life Sciences, 1987, 41, 527–544), circulatory insufficiency (J. LOSAY et al., 1977, Substance P, von Euler, U.S. and Pernow ed., 287–293, Raven Press, New York), gastrointestinal complaints (D. REGOLI et al., Trends Pharmacol. Sci., 1985, 6, 481–484), respiratory complaints (J. MIZRAHI et al., Pharmacology, 1982, 25, 39–50).

Endogenous ligands for neurokinin receptors have been described, such as substance P (SP), neurokinin A (NKA) (S. J. BAILEY et al., 1983, Substance P, P. Skrabanck ed., 16–17 Boole Press, Dublin) and neurokinin B (NKB) (S. P. WATSON, Life Sciences, 1983, 25, 797–808).

Neurokinin receptors have been recognised on numerous preparations, and are currently classified into three types: $NK_1$, $NK_2$ and $NK_3$. Whereas most preparations studied hitherto possess several types of receptors, such as guinea pig ileum ($NK_3$, $NK_2$ and $NK_3$), some of them appear to possess only one type, such as dog carotid artery ($NK_1$), rabbit pulmonary artery bereft of endothelium ($NK_2$) and rat portal vein ($NK_3$) (D. REGOLI et al., Trends Pharmacol. Sci., 1988, 9, 290–295 and Pharmacology, 1989, 38, 1–15).

A more precise characterisation of the different receptors is made possible by the recent synthesis of selective agonists. Thus, [$Sar^9$,Met-$(O_2)^{11}$]Sp, [$Nle^{10}$] $NKA_{4-10}$ and [Me $Phe^7$]NKB appear to exhibit a respective selectivity for $NK_1$, $NK_2$ and $NK_3$ receptors (see D. REGOLI, 1988 and 1989 cited above).

It has now been found that some aromatic amino compounds possess advantageous pharmacological properties when interacting with the neurokinin receptors, and are useful, in particular, for the treatment of any substance P- and neurokinin-dependent pathology, in particular analgesia and inflammation.

Thus, according to one of its aspects, the present invention relates to aromatic amino derivatives of formula:

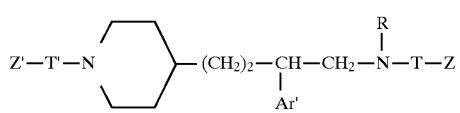

in which

Ar' represents a phenyl, unsubstituted or substituted one or more times with a halogen atom, preferably a chlorine or fluorine atom, with a $C_1-C_3$ alkyl, with a trifluoromethyl, with a $C_1-C_3$ alkoxy, with a hydroxyl; a thienyl, pyridyl or naphthyl group, the said groups being unsubstituted or substituted with a halogen, preferably a chlorine or fluorine atom, an indolyl group or a benzothienyl group;

R represents hydrogen, a methyl group or a group $(CH_2-)_n-L$, where n is an integer from 2 to 6 and L is hydrogen or an amino group;

Z and Z' represent, independently, a hydrogen atom or a group M or OM,

M represents hydrogen or a linear or branched $C_1-C_6$ alkyl; an α-hydroxybenzyl, an α-alkylbenzyl or a phenylalkyl in which the alkyl group contains 1 to 3 carbon atoms, unsubstituted, mono- or poly-substituted on the aromatic ring with a halogen, a hydroxyl, an alkoxy of 1 to 4 carbon atoms, an alkyl of 1 to 4 carbon atoms; a pyridylalkyl in which the alkyl group contains 1 to 3 carbon atoms; a naphthylalkyl in which the alkyl group contains 1 to 3 carbon atoms; a pyridylthioalkyl in which the alkyl group contains 1 to 3 carbon atoms; a styryl; a 1-methyl-2-imidazolylthioalkyl in which the alkyl group contains 1 to 3 carbon atoms; a 1-oxophenyl-3-indan-2-yl; an aromatic or heteroaromatic group, the said group being unsubstituted or substituted;

T' represents a bond, a —$CH_2$— group or a —C(O)— group;

T represents a group selected from

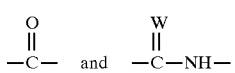

w being an oxygen or sulphur atom, with the limitation that
when Z' is hydrogen or OM, T' is other than a bond; and
when Z is hydrogen or OM, T is other than a group —C(W) —NH—, or one of their possible salts with inorganic or organic acids, or one of their quarternary ammonium salts.

The quaternary ammonium salts of the compounds of formula (I) are formed from the nitrogen atom of the piperidine; the group

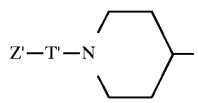

is then represented by the group:

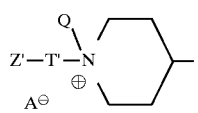

in which

Q represents a $C_1-C_6$ alkyl group or a benzyl group and $A^-$ represents an anion chosen from amongst chloride, bromide, iodide, acetate, methanesulphonate or para-toluenesulphonate.

In the present description, the alkyl and alkoxy groups are linear or branched.

The salts of the compounds of formula (I) according to the present invention comprise both those with inorganic or organic acids which permit a suitable crystallisation or separation of the compounds of formula (I), such as picric acid or oxalic acid or an optically active acid, for example a mandelic or camphorsulphonic acid, and those which form pharmaceutically acceptable salts such as the hydrochloride, hydrobromide, sulphate, hydrogen sulphate, dihydrogen phosphate, methanesulphonate, methyl sulphate, maleate, fumarate, 2-naphthalenesulphonate, glycolate, gluconate, citrate or isethionate.

In particular, in the formula (I), Z and/or Z' represents a mono-, di- or tricyclic aromatic or heteroaromatic group, capable of bearing one or more substituents, in which a carbon atom of the aromatic carbocycle or aromatic heterocycle is linked directly to the group T or to the group T'.

More especially, the radicals Z and/or Z' can be a phenyl or benzyl group, which can be unsubstituted or optionally contain one or more substituents.

When Z and/or Z' are a phenyl or benzyl group, these groups can preferably be mono- or disubstituted, in particular 2,4-disubstituted, but also, for example, 2,3-, 4,5-, 3,4- or 3,5-disubstituted; they can also be trisubstituted, in particular 2,4,6-trisubstituted, but also, for example, 2,3,4-, 2,3,5-, 2,4,5- or 3,4,5-trisubstituted; tetra-substituted, for example 2,3,4,5-tetrasubstituted; or pentasubstituted. The substituents of the phenyl or benzyl groups can be: F;, Cl; Br; I, CN; OH; $NH_2$; NH—CO—$NH_2$; $NO_2$; $CONH_2$; $CF_3$; $C_1$–$C_{10}$ and preferably $C_1$–$C_4$ alkyl, methyl or ethyl being preferred, as well as, for example, n-propyl, isopropyl, n-butyl, isobutyl, sec-butyl, tert-butyl, pentyl or n-pentyl, hexyl or n-hexyl, heptyl or n-heptyl, octyl or n-octyl, nonyl or n-nonyl as well as decyl or n-decyl; alkenyl containing 2 to 10 and preferably 2–4 carbon atoms, for example vinyl, allyl, 1-propenyl, isopropenyl, butenyl or 1-buten-1-, -2-, -3- or -4-yl, 2-buten-1-yl, 2-buten-2-yl, pentenyl, hexenyl or decenyl; alkynyl containing 2 to 10 and preferably 2–4 carbon atoms, for example ethynyl, 1-propyn-1-yl, propargyl, butynyl or 2-butyn-1-yl, pentynyl, decynyl; cycloalkyl containing 3 to 8 and preferably 5 or 6 carbon atoms, cyclopentyl or cyclohexyl being preferred, as well as, for example, cyclopropyl, cyclobutyl, 1-, 2- or 3-methylcyclopentyl, 1-, 2-, 3- or 4-methylcyclohexyl, cycloheptyl or cyclooctyl; bicycloalkyl containing 4 to 11 and preferably 7 carbon atoms, exo- or endo-2-norbornyl being preferred, as well as, for example, 2-isobornyl or 5-camphyl; hydroxyalkyl containing 1 to 5 and preferably 1–2 carbon atoms, hydroxymethyl and 1- or 2-hydroxyethyl being preferred, as well as, for example, 1-hydroxy-1-propyl, 2-hydroxy-1-propyl, 3-hydroxy-1-propyl, 1-hydroxy-2-propyl, 1-hydroxy-1-butyl, 1-hydroxy-1-pentyl; alkoxy containing 1 to 10 and preferably 1–4 carbon atoms, methoxy or ethoxy being preferred, as well as, for example, n-propoxy, isopropoxy, n-butoxy, isobutoxy, sec-butoxy, tert-butoxy, pentyloxy, hexyloxy, heptyloxy, octyloxy, nonyloxy or decyloxy; alkoxyalkyl containing 2 to 10 and preferably from 2 to 6 carbon atoms, for example alkoxymethyl or alkoxyethyl such as methoxymethyl or 1- or 2-methoxyethyl, 1- or 2-n-butoxyethyl, 1- or 2-n-octyloxyethyl; alkoxyalkoxy-alkyl containing from 3 to 10 and preferably from 4 to 7 carbon atoms, for example alkoxyalkoxymethyl, for example 2-methoxyethoxymethyl, 2-ethoxyethoxymethyl or 2-isopropoxyethoxymethyl, alkoxyalkoxyethyl, for example 2-(2-methoxyethoxy)ethyl or 2-(2-ethoxyethoxy)ethyl; alkoxyalkoxy containing from 2 to 10 and preferably from 3 to 6 carbon atoms, for example 2-methoxyethoxy, 2-ethoxyethoxy or 2-n-butoxyethoxy; alkenyloxy containing 2 to 10 and preferably 2 to 4 carbon atoms, allyloxy being preferred, as well as, for example, vinyloxy, propenyloxy, isopropenyloxy, butenyloxy such as 1-buten-1-, -2-, -3- or -4-yloxy, 2-buten-1-yloxy, 2-buten-2-yloxy, pentenyloxy, hexenyloxy or decenyloxy; alkenyloxyalkyl containing from 3 to 10 and preferably 3–6 carbon atoms, for example allyloxymethyl; alkynyloxy containing from 2 to 10 and preferably from 2 to 4 carbon atoms, propargyloxy being preferred, as well as, for example, ethynyloxy, 1-propyn-1-yloxy, butynyloxy or 2-butyn-1-yloxy, pentynyloxy or decynyloxy; alkynyloxyalkyl containing from 3 to 10 and preferably 3 to 6 carbon atoms, for example ethynyloxymethyl, propargyloxymethyl or 2-(2-butyn-1-yloxy)ethyl; cycloalkoxy containing 3 to 8 and preferably 5 or 6 carbon atoms, cyclopentyloxy or cyclohexyloxy being preferred, as well as, for example, cyclopropyloxy, cyclobutyloxy, 1-, 2- or 3-methylcyclopentyloxy, 1-, 2-, 3- or 4-methylcyclohexyloxy, cycloheptyloxy or cyclooctyloxy; alkylthio containing from 1 to 10 and preferably 1 to 4 carbon atoms, methylthio or ethylthio being preferred, as well as, for example, n-propylthio, isopropylthio, n-butylthio, isobutylthio, sec-butylthio, tert-butylthio, pentylthio, hexylthio, octylthio, nonylthio or decylthio; alkylthioalkyl containing from 2 to 10 and preferably 2 to 6 carbon atoms, for example methylthiomethyl, 2-methylthioethyl or 2-n-butylthioethyl; acylamino, namely alkanoylamino containing from 1 to 7 and preferably 1 to 4 carbon atoms, formylamino and acetylamino being preferred, as well as propionylamino, butyrylamino, isobutyrylamino, valerylamino, caproylamino, heptanoylamino, as well as aroylamino or benzoylamino; acylaminoalkyl, preferably alkanoylaminoalkyl containing from 2 to 8 and preferably 3 to 6 carbon atoms, such as formylaminoethyl, acetylaminoethyl, propionylaminoethyl, n-butyrylaminoethyl, formylaminopropyl, acetylaminopropyl, propionylaminopropyl, formylaminobutyl, acetylaminobutyl, as well as propionylaminobutyl, butyrylaminobutyl; acyloxy containing from 1 to 6 and preferably 2 to 4 carbon atoms, acetyloxy, propionyloxy or butyryloxy being preferred, as well as, for example, formyloxy, valeryloxy, caproyloxy; alkoxycarbonyl containing from 2 to 5 and preferably 2 and 3 carbon atoms, methoxycarbonyl and ethoxycarbonyl being preferred, as well as, for example, n-propoxycarbonyl, isopropoxycarbonyl, n-butoxycarbonyl, isobutoxycarbonyl, sec-butoxycarbonyl or tert-butoxycarbonyl; cycloalkoxycarbonyl containing from 4 to 8 and preferably 6 or 7 carbon atoms, cyclopentyloxycarbonyl, cyclohexyloxycarbonyl being preferred, as well as cyclopropyloxycarbonyl, cyclobutyloxycarbonyl or cycloheptyloxycarbonyl; alkylaminocarbonylamino containing from 2 to 4 carbon atoms, such as methylaminocarbonylamino, ethylaminocarbonylamino, propylaminocarbonylamino; dialkylaminocarbonylamino containing from 3 to 7 and preferably 3 to 5 carbon atoms, preferably dimethylaminocarbonylamino, as well as di-n-propylaminocarbonylamino, diisopropylaminocarbonylamino; pyrrolidinocarbonylamino; piperidinocarbonylamino; cycloalkylaminocarbonylamino containing from 4 to 8 and preferably 6 or 7 carbon atoms, cyclopentylaminocarbonylamino, cyclohexylaminocarbonylamino being preferred, as well as cyclopropylaminocarbonylamino, cyclobutylaminocarbonylamino, cycloheptylaminocarbonylamino; alkylaminocarbonylaminoalkyl containing from 3 to 9 and preferably 4 to 7 carbon atoms, methylaminocarbonylaminoethyl, ethylaminocarbonylaminoethyl, ethylaminocarbonylaminopropyl, ethylaminocarbonylaminobutyl being preferred, as well as, for example, methylaminocarbonylaminomethyl, n-propylaminocarbonylaminobutyl, n-butylaminocarbonylaminobutyl; dialkylaminocarbonylaminoalkyl containing from 4 to 11 carbon atoms, for example dimethylaminocarbonylaminomethyl, diethylaminocarbonylaminoethyl, diethylaminocarbonylaminopropyl, diethylaminocarbonylaminobutyl, pyrrolidinocarbonylaminoethyl, piperidinocarbonylaminoethyl; cycloalkylaminocarbonylaminoalkyl containing from 5 to 12 and preferably 8 to 11 carbon atoms, cyclopentylaminocarbonylaminoethyl, cyclopentylaminocarbonylaminopropyl, cyclopentylaminocarbonylaminobutyl, cyclohexylaminocarbonylaminoethyl, cyclohexylaminocarbonylaminopropyl and cyclohexylaminocarbonylaminobutyl being preferred, as well as, for example, cyclopropylaminocarbonylaminoethyl, cycloheptylaminocarbonylaminoethyl; alkoxycarbonylaminoalkyl containing from 3 to 12 and preferably 4 to 9 carbon atoms, methoxycarbonylaminoethyl, ethoxycarbonylaminoethyl, n-propoxycarbonylaminoethyl, isopropoxycarbonylaminoethyl, n-butoxycarbonylaminoethyl, isobutoxycarbonylaminoethyl, sec-butoxycarbonylaminoethyl, tert-butoxycarbonylaminoethyl, ethoxycarbonylaminopropyl, n-butoxycarbonylaminopropyl, ethoxycarbonylaminobutyl, n-butoxycarbonylaminobutyl being preferred, as well as, for example, n-propoxycarbonylaminopropyl, n-propoxycarbonylaminobutyl, isopropoxycarbonylaminobutyl; cycloalkoxycarbonylaminoalkyl containing from 5 to 12 and preferably 8 to 11 carbon atoms, cyclopentyloxycarbonylaminoethyl, cyclopentyloxycarbonylaminopropyl, cyclopentyloxycarbonylaminobutyl, cyclohexyloxycarbonylaminoethyl, cyclohexyloxycarbonylaminopropyl, cyclohexyloxycarbonylaminobutyl being preferred, as well as, for example, cyclopropyloxycarbonylaminomethyl, cycloheptyloxycarbonylaminoethyl; carbamoylalkyl containing from 2 to 5 and preferably 2 carbon atoms, preferably carbamoylmethyl, as well as carbamoylethyl, carbamoylpropyl, carbamoylbutyl; alkylaminocarbonylalkyl containing from 3 to 9 and preferably 3 to 6 carbon atoms, methylaminocarbonylethyl, ethylaminocarbonylmethyl, n-propylaminocarbonylmethyl, isopropylaminocarbonylmethyl, n-butylaminocarbonylmethyl, isobutylaminocarbonylmethyl, sec-butylaminocarbonylmethyl, tertbutylaminocarbonylmethyl being preferred, as well as, for example, ethylaminocarbonylethyl, ethylaminocarbonylpropyl, ethylaminocarbonylbutyl, n-propylaminocarbonylbutyl, n-butylaminocarbonylbutyl; dialkylaminocarbonylalkyl containing from 4 to 11 and preferably 4 to 8 carbon atoms, dimethylaminocarbonylmethyl, diethylaminocarbonylmethyl, di-n-propylaminocarbonylmethyl, as well as, for example, diethylaminocarbonylethyl, diethylaminocarbonylpropyl, diethylaminocarbonylbutyl; pyrrolidinocarbonylmethyl, piperidinocarbonylmethyl; piperidinocarbonylethyl; cycloalkylaminocarbonylalkyl containing from 5 to 12 and preferably 7 or 8 carbon atoms, cyclopentylaminocarbonylmethyl and cyclohexylaminocarbonylmethyl being preferred, as well as, for example, cyclopropylaminocarbonylmethyl, cyclobutylaminocarbonylmethyl, cycloheptylaminocarbonylmethyl, cyclohexylaminocarbonylethyl, cyclohexylaminocarbonylpropyl, cyclohexylaminocarbonylbutyl; al.kylaminocarbonylalkoxy containing from 3 to 10 and preferably 3 to 5 carbon atoms, methylaminocarbonyl-methoxy being preferred, as well as, for example, methylaminocarbonylethoxy, methylaminocarbonylpropoxy; dialkylaminocarbonylalkoxy containing from 4 to 10 and preferably 4 to 7 carbon atoms, such as dimethylaminocarbonylmethoxy, diethylaminocarbonylethoxy, (1-piperidyl)carbonylmethoxy; cycloalkylaminocarbonylalkoxy containing from 5 to 11 and preferably 7 or 8 carbon atoms, such as cyclopentylaminocarbonylmethoxy, cyclohexylaminocarbonylmethoxy.

The groups Z and Z' are advantageously a phenyl group; a benzyl group; a benzoyl group; a phenylthioalkyl group in which the alkyl is a $C_1$–$C_3$ group; a naphthyl group.

The phenyl group Z or Z' is preferably mono- or disubstituted with a halogen or with a $C_1$–$C_4$ alkoxy group, the group 2,4-dichlorophenyl being particularly preferred.

The radicals Z or Z' can also represent a bicyclic aromatic group such as 1- or 2-naphthyl; 1-, 2-, 3-, 4-, 5-, 6-, 7-indenyl; in which one or more bonds may be hydrogenated, it being possible for the said groups to be unsubstituted or optionally to contain one or more substituents such as a halogen, and more particularly a fluorine atom, alkyl, phenyl, cyano, hydroxyalkyl, hydroxyl, oxo, alkylcarbonylamino, alkoxycarbonyl and thioalkyl groups, in which groups the alkyls are $C_1$–$C_4$ groups.

The radicals Z or Z' can also be a pyridyl, thiadiazolyl, indolyl, indazolyl, imidazolyl, benzimidazolyl, quinolyl, benzotriazolyl, benzofuranyl, benzothienyl, benzothiazolyl, benzisothiazolyl, isoquinolyl, benzoxazolyl, benzisoxazolyl, benzoxazinyl, benzodioxinyl or pyridinyl, isoxazolyl, benzopyranyl, thiazolyl, thienyl, furyl, pyranyl, chromenyl, isobenzofuranyl, pyrrolyl, pyrazolyl, pyrazinyl, pyrimidinyl, pyridazinyl, indolizinyl, phthalazinyl, quinazolinyl, acridinyl, isothiazolyl, isochromanyl or chromanyl, in which one or more double bonds may be hydrogenated, it being possible for the said groups to be unsubstituted or optionally to contain one or more substituents such as alkyl, phenyl, cyano, hydroxyalkyl, hydroxyl, alkylcarbonylamino, alkoxycarbonyl and thioalkyl groups, in which groups the alkyls are $C_1$–$C_4$ groups.

According to another of its aspects, the present invention relates to a process for the preparation of differently substituted aromatic amino compounds of formula (I) and their salts.

Firstly, the N-protecting and O-protecting derivative of 1-hydroxy-2-(4-piperidinyl)ethane is prepared according to the conventional and usual methods using protecting groups well-known by the person skilled in the art for the N-protecting groups or for the O-protective groups, according to Scheme 1 which follows, to obtain the protecting amino alcohol which is a novel intermediate being part of the invention.

SCHEME 1

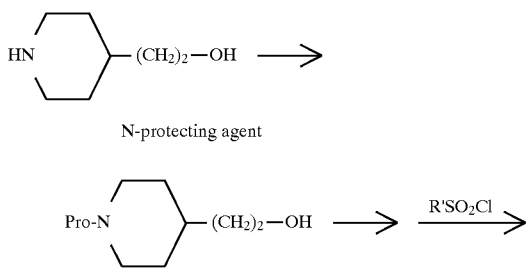

-continued
SCHEME 1

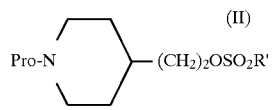
(II)

in which:

Pro denotes an N-protecting group

R' represents a $C_1$–$C_4$ alkyl group, a phenyl group or a tolyl group, preferably para-tolyl.

The compound of formula (II) is prepared starting from 2-(4-piperidinyl)ethanol, a commercially available product.

In the present description, the terms "N-protecting group," "N-protecting" and "N-deprotection" or simply "deprotection" are used.

The term "N-protecting group" indicates an amino-protecting group of the type used in peptide or nucleotide chemistry, for example an acyl group, such as formyl, acetyl, propionyl; an alkoxycarbonyl group, such as t.-butoxycarbonyl (BOC); an alkoxyalkylcarbonyl group, such as methoxypropionyl; a substituted alkoxycarbonyl group, such as trichloroethoxycarbonyl; a substituted alkylcarbonyl group, such as monochloromethylcarbonyl, monochloroethylcarbonyl, dichloroethylcarbonyl, trichloromethylcarbonyl, trichloropropylcarbonyl; an aralkyloxycarbonyl group, such as benzyloxycarbonyl; a substituted aralkyloxycarbonyl group, such as 4-nitrobenzyloxycarbonyl or aroyl such as benzoyl, 2,4-dichlorobenzoyl or 4-fluoro-1-naphthyl carbonyl. The term "N-protecting" also includes aralkyl groups such as, for example, a benzyl group, unsubstituted or substituted, for example, with 1 or 2 halogen atoms, preferably chlorine or with 1 or 2 alkoxy groups, preferably methoxy; a diphenylmethyl (or benzhydryl) group, a substituted diphenylmethyl group such as di(4-methoxy)diphenylmethyl (or dimethoxybenzhydryl), a triphenylmethyl (or trityl) group, a substituted triphenylmethyl group, such as 4-methoxyphenyl-diphenylmethyl (or methoxytrityl) or di(4-methoxyphenyl) phenylmethyl (or dimethoxytrityl). The term "N-protecting" refers to the product which contains the amine protected with an N-protecting group such as defined above.

The term "N-deprotection" or simply "deprotection" indicates the elimination of the N-protecting group and the formation of the free amine according to the conventional methods well-known by the person skilled in the art, for example by reduction or by acid hydrolysis according to the N-protecting group to be eliminated.

The process for the preparation of compounds (I) is illustrated by Scheme 2

SCHEME 2

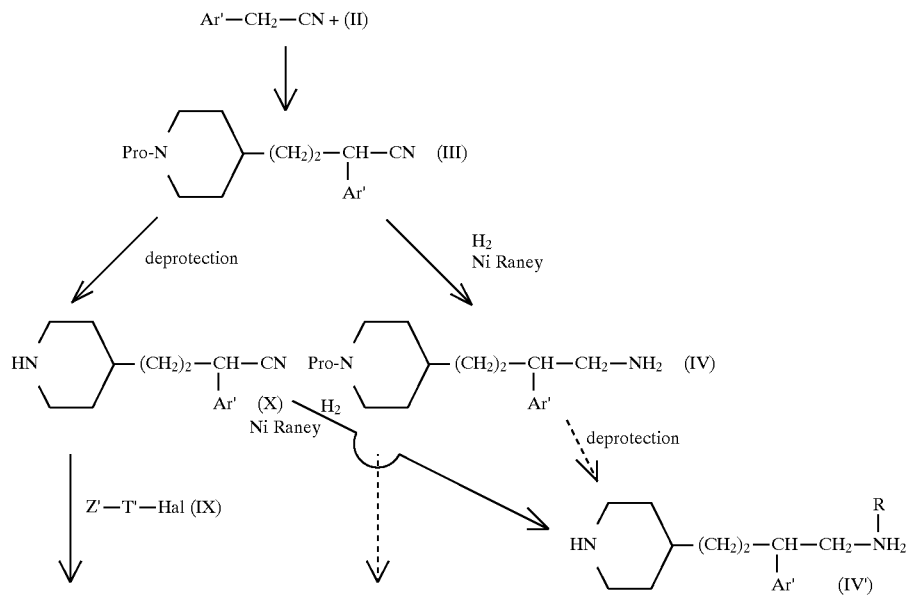

-continued
SCHEME 2

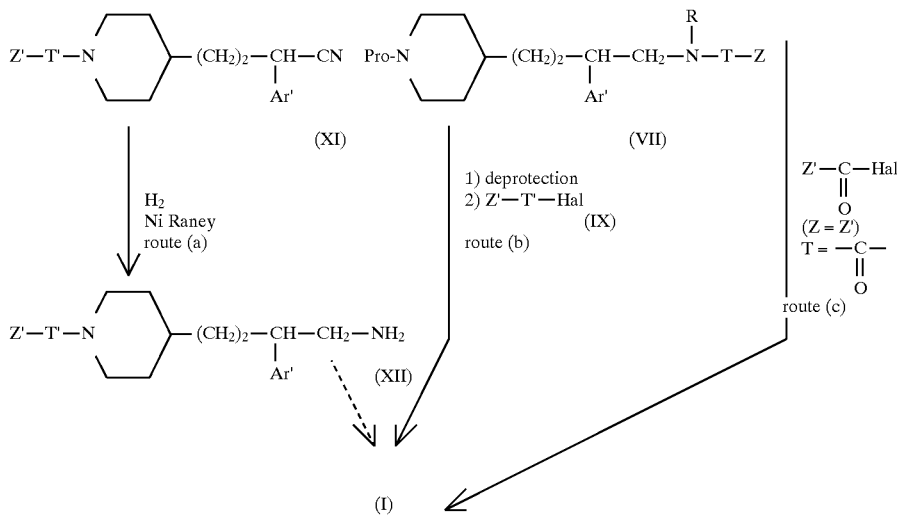

In this scheme, the compounds of formulae VII and I are indicated as being directly obtained from the compounds IV (route (b)), XII (route (a)) and IV' (route (c)). In reality, when R is a substituent other than hydrogen, the said substituent is introduced on the amine of the compounds XII (route (a)), IV (route (b)) and IV' (route (c)) according to the methods described in detail below. The same remark applies to schemes 3 and 4.

The starting compounds of formula (III) are prepared starting from nitrites of formula:

in which Ar' is as defined above, nitriles which are commercial products or products prepared according to known methods, by reaction with a compound of formula (II); then the N-protected aminonitrile of formula (III) is treated according to one of the synthesis routes (a), (b) or (c), which use the same reactions but in different orders.

Thus, according to route (b), the nitrile (III) is subjected to catalytic hydrogenation in the presence of a catalyst such as, for example, Raney nickel to yield the amine of formula:

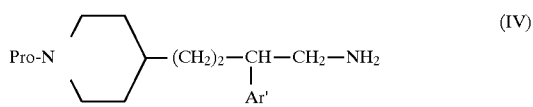

which is a novel intermediate being part of the invention and which is then functionalised either with a functional derivative of an acid of formula:

in which Z is as defined above, when a compound of formula (I) is to be prepared in which T is —CO—, or with an iso(thio)cyanate of formula:

in which W and Z are as defined above, when a compound of formula (I) is to be prepared in which T is —C(W)—NH—, to yield the derivative of formula:

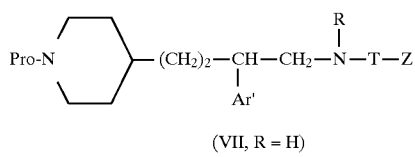

which is a novel intermediate being part of the invention and which is then deprotected to lead to the free amine of formula:

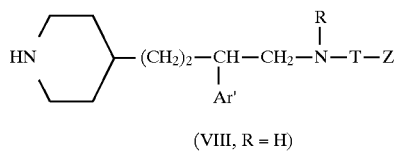

in which Ar', T and Z are as defined above, then this amine is added onto a halogenated derivative of formula:

in which Z' and T' are as defined above and where Hal represents a halogen, more particularly a chlorine or bromine atom, to lead to compounds (I) according to the invention.

According to the synthesis route (a), the aminonitrile (III) is deprotected according to the usual methods to lead to the free aminonitrile of formula:

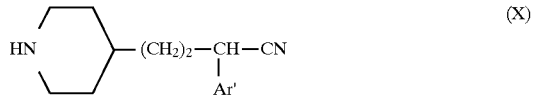

in which Ar' is as defined above, and onto which is added the halogenated derivative (IX) to lead to the nitrile of formula:

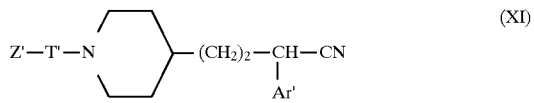

in which Z', T', Ar' are as defined above. This compound (XI) is then hydrogenated in the presence of a catalyst such as Raney nickel to yield the corresponding amino derivative of formula:

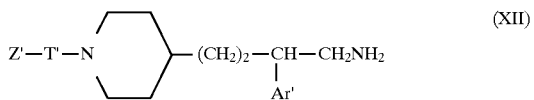

which is a novel intermediate being part of the invention and which is then functionalised to yield the compound (I) according to the invention proceeding in the same fashion as above for the preparation of compounds (I) starting from intermediates (VII), that is to say by reacting:

either with a functional derivative of an acid of formula:

in which Z is as defined above, when a compound of formula (I) is to be prepared in which T is —CO—, or with an iso(thio)cyanate of formula:

in which W and Z are as defined above when a compound of formula (I) is to be prepared in which T is —C(W)—NH—, to yield the derivative (I) where R is H.

As the functional derivative of the acid (V), the acid itself is used, appropriately activated, for example, by cyclohexylcarbodiimide or by N-benzotriazolyl oxytrisdimethylaminophosphonium hexafluorophosphate (BOP), or else one of the functional derivatives which react with the amines, for example an anhydride, a mixed anhydride, the chloride or an activated ester. When Z is a group OM, the acid concerned is carbonic acid and, as a functional derivative, the monochloride, that is to say a chloroformate Cl—CO—OM, is used.

According to the synthesis route (c), the nitrile (III) is subjected to hydrogenation as in route (b), then the compound (IV) obtained is deprotected to form the corresponding compound (IV') which is then reacted with the halogenated derivative Z'—C(O)—Hal to form the compound of formula (I) in which Z=Z'.

In a variant, the compound of formula (IV') can be obtained starting from the compound of formula (X) by hydrogenation in the presence of a catalyst, such as Raney nickel.

The preparation of the compounds of formula (VII) or (I), where R is other than hydrogen is carried out according to methods known per se.

When it is desired to prepare the compounds of Formula (IV) or (XII) in which R is methyl, the free amine, obtained by hydrogenation of the nitrites (III) or (XI) as described above, is treated with a chloroformate, for example with the chloroformate of formula Cl—CO—OAlk, where Alk is a $C_1$–$C_3$ alkyl, preferably ethyl, to obtain the carbamates of formula:

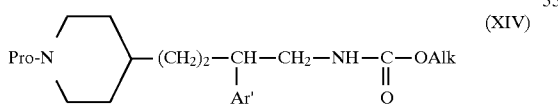

or

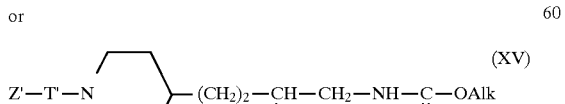

which are then reduced by known means, such as the action of a reducing agent such as, for example, a metallic hydride, such as sodium aluminium hydride or lithium aluminium hydride, or by a boron hydride, such as borane dimethylsulphide. The reduction is carried out in a solvent, such as ether or toluene, at a temperature between room temperature and 60° C. The methylamines thus obtained of formula:

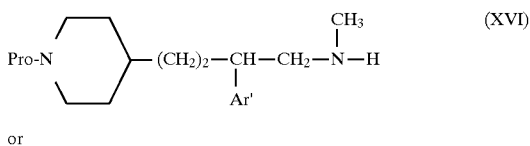

or

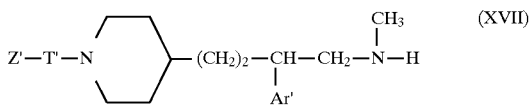

are isolated according to the usual methods.

The methylamine of formula (XVI) above can be deprotected to give piperidine of formula:

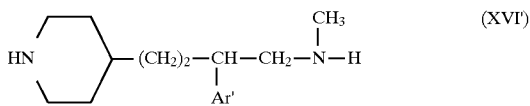

Starting from the compounds of formulae (XVI), (XVI') and (XVII), the N-substituted compounds are prepared in the same manner as described in schemes 2 to 4 starting, respectively, from the compounds of formulae (IV) (route (b)), IV' (route (c)) and (XII) (route (a)).

To prepare the compounds of formula (IV) or (XII) in which R is a group —$(CH_2)_n$—L, where n and L are as defined above, the free amine, obtained by hydrogenation of the nitrile (III) or (XI) as described above, is treated with a reactive functional derivative, as defined above, of the acid of formula:

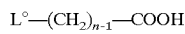

in which L° is hydrogen or a protected amino group, to obtain the amides of formula:

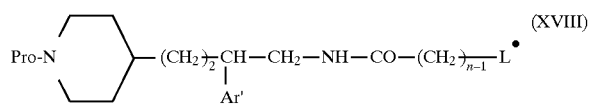

or

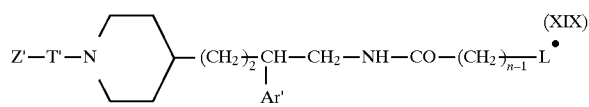

The amides (XVIII) or (XIX), by reduction under the same conditions as those described above for the nitrites (III) or (XI), give the desired compound of formula:

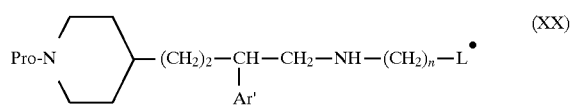

or

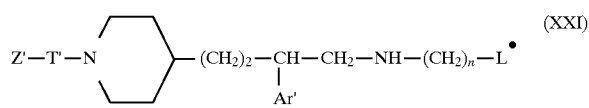

The alkylamines of formula (XX) above can be partially deprotected to give the piperidine of formula:

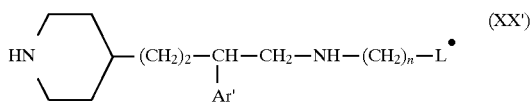

Starting from the compounds of formula (XX), (XX') and (XXI) above, the N-substituted compounds are prepared in the same manner as, described further above in schemes 2 to 4, starting, respectively, from the compounds (IV) (route (b)), (IV') (route (c)) and (XII) (route (a)).

The N-protecting groups optionally present in the group R when L is an amino group are the conventional N-protecting groups well-known to the person skilled in the art and preferably those which can be eliminated by acid hydrolysis, such as the trityl group, the methoxytrityl group and BOC.

The preparation of the compounds (VII) or (I) is illustrated by schemes 3 and 4 shown in detail below.

(N-benzotriazolyloxytrisdimethylaminophosphonium hexafluorophosphate), then by adding the acid (V) in the presence of an organic base such as, for example, triethylamine, to a solvent such as dichloromethane or dimethylformamide, at room temperature, the compounds (I$_1$) obtained being isolated and purified according to the usual methods, for example chromatography or recrystallisation.

(IV) or (XII) can also be reacted with an iso(thio)cyanate W=C=N—Z (VI) in an anhydrous inert solvent such as, for example, benzene, overnight at room temperature and the reaction mixture can then be treated according to the usual methods to obtain the compounds (I$_2$).

The products of formula (I) thus obtained are isolated, in the form of free base or of salt, according to the conventional techniques.

When the compound of formula (I) is obtained in the form of free base, the salification is performed by treatment with

SCHEME 3

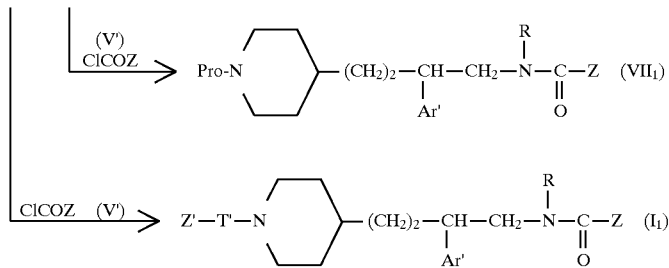

SCHEME 4

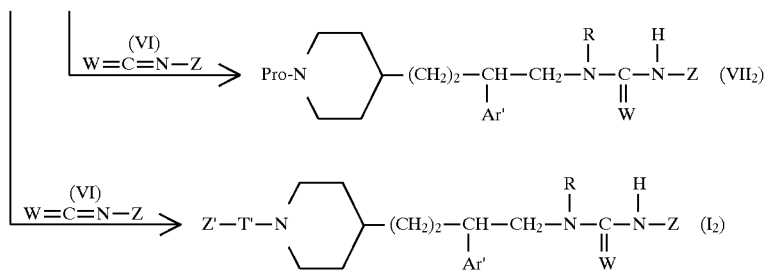

The acid chloride Cl—CO—Z is therefore considered as a reactive functional derivative of the acid (V). The reaction with the acid choride is performed in an inert solvent, such as dichloromethane or benzene in the presence of a base such as, for example, triethylamine, at room temperature.

In the particular case where Z=OM, the reaction of the compounds (IV) or (XII) with the chloroformate of formula:

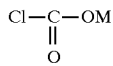

is performed according to the usual methods.

When Z is other than OM, another functional derivative can be used or the process can start from the free acid (V) by carrying out a coupling of (IV) or (XII) with BOP the chosen acid in an organic solvent. By treatment of the free base, dissolved, for example, in an alcohol such as isopropanol, with a solution of the chosen acid in the same solvent, the corresponding salt is obtained and is isolated according to the conventional techniques. Thus, for example, the hydrochloride, hydrobromide, sulphate, hydrogen sulphate, dihydrogen phosphate, methanesulphonate, oxalate, maleate, fumarate or the 2-napthalenesulphonate are prepared.

At the end of the reaction, the compounds of formula (I) can be isolated in the form of one of their salts, for example the hydrochloride or the oxalate; in this case, if it is necessary, the free base can be prepared by neutralisation of the said salt with an inorganic or organic base, such as sodium hydroxide or triethylamine or with an alkaline metal carbonate or bicarbonate, such as sodium or potassium carbonate or bicarbonate.

The quarternary ammonium salts formed with the nitrogen of the piperidine are prepared by reaction of the free bases of the compounds (I), for which the other amino functions optionally present are N-protected by a customary N-protecting group, with an excess of alkylating agent of formula:

A—Q in which A represents a leaving group and is such as defined above for (I), preferably a chloride or an iodide and Q is such as defined above for (I), and the reaction mixture is heated in a solvent, for example chosen from amongst dichloromethane, chloroform, acetone or acetonitrile, at a temperature between room temperature and the reflux temperature of the solvent for one to several hours to obtain, after treatment according to the customary methods and after deprotection if necessary, a mixture of the axial and equatorial conformers of the quaternary ammonium salts.

Preferably, $A^{\ominus}$ represents an iodide which can be exchanged for another anion or for a pharmacologically acceptable anion, for example a chloride, by elution of the compound (I) on anion exchange resin, for example Amberlite IRA68® or Duolite A375®.

The conformers are separated according to the customary methods, for example by chromatography or by recrystallisation.

Each of the axial or equatorial conformers of the compounds (I) in the form of racemates or in the form of optically pure R or S enantiomers are part of the invention.

The resolution of the racemic mixtures (I) enables the enantiomers which are part of the invention to be isolated.

The invention also relates to the intermediates employed in the process described above for obtaining the compounds of the invention (see scheme 2).

These intermediates are the arylalkylpiperidines of formula:

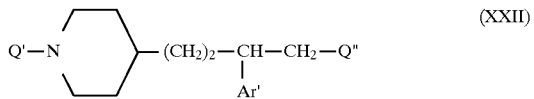
(XXII)

in which:

Ar' is as defined above and either Q' is hydrogen or an N-protecting group and Q" is an amino group or a group:

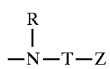

where R and T and Z are as defined above, or Q' is a group:

Z'—T'— where Z', and T' are as defined above and

Q" is an amino group and the acid addition salts of the said aralkylpiperidines when the latter are basic.

The synthesis intermediates of formula

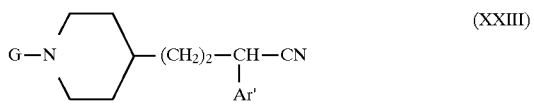
(XXIII)

in which G is hydrogen, a protecting group (Pro) or a group of formula Z'—T'—in which Z' and T' are as defined above, Ar' has the meaning given for the compounds of formula I, are also novel compounds which are part of the scope of the invention.

All the synthesis intermediates carried out in the process according to the invention can be isolated, according to the conventional methods well known to the person skilled in the art, in the form of their salts.

The compounds according to the invention were subjected to niochemicaL tests.

The compounds (I) and their salts showed binding properties specific to the receptor of substance P in tests carried out on rat cortex membranes and IM9 lymphoblastic cells, according to M.A. CASCIERI et al., J. Biol. Chem., 1983, 258, 5158–5164 and D. D. PAYA et al.,J. Immunol., 1984, 133, 3260–3265.

The compounds according to the invention inhibit the immobilisation of substance P to its receptor.

Thus, for example, compounds 3, 7 and 11 inhibit the binding of substance P with Kis, of 23,15 and 30 nanomolar, respectively.

The compounds of the present invention are poorly toxic. Their toxicity is compatible with their use as active principles of medicaments. These medicaments are preferable suitable for the treatment of pain and inflammation.

The compounds of the present invention are generally administered in the form of dosage units. The said dosage units are preferably formulated in pharmaceutical compositions in which the active principle is mixed with a pharmaceutical excipient.

Thus, according to another of its aspects, the present invention relates to pharmaceutical compositions containing as active principle a compound of formula (I) or one of its pharmaceutically acceptable salts.

The compounds of formula (I) above and their pharmaceutically acceptable salts can be used in daily doses of 0.01 to 100 mg per kilo of body weight of the mammal to be treated, preferably in daily doses of 0.1 to 50 mg/kg. In the human being, the dose can preferably vary from 0.5 to 4000 mg per day, more particularly from 2.5 to 1000 mg according to the age of the subject to be treated or the type of treatment: prophylactic or curative.

In the pharmaceutical compositions of the present invention for oral, sublingual, subcutaneous, intramuscular, intravenous, transdermal, local or rectal administration, the active principles may be administered in single-dose administration forms, mixed with conventional pharmaceutical carriers, to animals and to human beings. Suitable single-dose administration forms comprise oral forms such as tablets, gelatin capsules, powders, granules and solutions or suspensions to be taken by mouth, forms for sublingual and buccal administration, forms for subcutaneous, intramuscular, intravenous, intranasal or intraocular administration and forms for rectal administration.

When a solid composition is prepared in the form of tablets, the principal active principle is mixed with a pharmaceutical vehicle such as gelatin, starch, lactose, magnesium stearate, talc, gum arabic or the like. The tablets may be coated with sucrose or other suitable substances, or alternatively treated in such a way that they have sustained or delayed activity and continuously release a predetermined quantity of active principle.

A preparation in the form of gelatin capsules is obtained by mixing the active principle with a diluent and pouring the mixture obtained into soft or hard gelatin capsules.

A preparation in the form of a syrup or elixir can contain the active principle together with a sweetener, preferably having zero energy content, and methylparaben and propylparaben as antiseptic, as well as an agent imparting flavour and a suitable colouring.

The water-dispersible powders or granules can contain the active principle mixed with dispersing agents or wetting agents or suspending agents such as polyvinylpyrrolidone, as well as with sweeteners or flavour correctors.

For rectal administration, suppositories which are prepared with binders melting at rectal temperature, for example cocoa butter or polyethylene glycols, are employed.

For parenteral, intranasal or intraocular administration, aqueous suspensions, isotonic saline solutions or sterile and injectable solutions which contain pharmacologically compatible dispersing agents and/or wetting agents, for example propylene glycol or butylene glycol, are used.

For administration by inhalation, an aerosol containing, for example, sorbitan trioleate or oleic acid, as well as trichlorofluoromethane, dichlorodifluoromethane, dichlorotetrafluoroethane or any other biologically compatible propellent gas, is used.

The active principle may also be formulated in the form of microcapsules, where appropriate with one or more carriers or additives.

The abovementioned compositions may also contain other active products such as, for example, bronchodilators, antitussives or antihistaminics.

The examples which follow illustrate the invention without, however, limiting it.

The melting or decomposition points, M.p., were measured on a Koffler heating block. The $^{13}C$ nuclear magnetic resonance spectra were performed at 50 MHz in dimethyl sulphoxide.

EXAMPLE 1

N-[4-(1-benzyl-4-piperidinyl)-2-(3,4-dichlorophenyl)-butyl]-4-fluoronaphtalene carboxamide hydrochloride

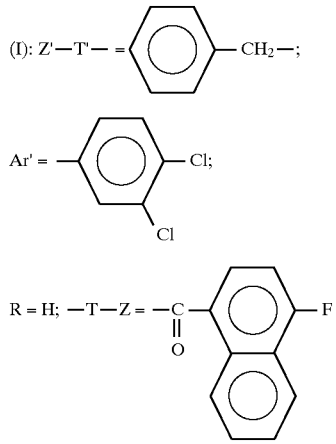

This compound is prepared by route (a) of scheme 2.
A) Preparation of 4-(2-mesyloxy-1-ethynyl)-1-tert-butoxycarbonylpiperidine.

65 g of 1-hydroxy-2-(4-piperidinyl)ethane are dissolved in a mixture of 250 ml of dioxane and 60 ml of water. 120 g of di-tert-butyl dicarbonate are added dropwise. The addition keeps the temperature of the reaction mixture at 50°–60° C. The addition completed, the reaction mixture is heated to 80° C. and the solvent is then concentrated in vacuo. The residue is taken up in ether and washed successively three times with water and then with a saturated NaCl solution. The ethereal phase is separated after settling has taken place, dried over $Na_2SO_4$ and concentrated.

110.2 g of a yellowish oil are obtained.

52.5 g of the oil prepared above and 26.6 g of triethylamine are dissolved in 300 ml of dichloromethane. The solution is cooled in ice and then 28.32 g of mesyl chloride dissolved in 5 ml of dichloromethane are added dropwise. The addition completed, the reaction mixture is heated under reflux for two hours.

The solvent is concentrated in vacuo, the residue is taken up in ethyl acetate and then washed successively with water and with a saturated NaCl solution, and the organic phase is separated, dried over $Na_2SO_4$ and concentrated in vacuo.

The residue is taken up in a mixture of 70 ml of ethyl acetate and 140 ml of hexane. The crystals are separated by filtration.

m=64 g
M.p.=91° C.
B) 1-(3,4-Dichlorophenyl)-3-(4-piperidinyl)-1-cyanopropane.

1.74 g of 55% sodium hydride suspended in oil are suspended in 150 ml of tetrahydrofuran and cooled to 5° C. 11.16 g of 3,4-dichlorophenylacetonitrile and 12.28 g of the amine prepared above according to A) dissolved in 150 ml of tetrahydrofuran are added dropwise. The reaction mixture is stirred overnight at room temperature and then heated under reflux for 30 minutes. The solvent is concentrated in vacuo, the residue is taken up in a pH=2 buffer solution and the mixture is extracted with ether. The ethereal phase is washed successively with water and with a saturated NaCl solution, dried over $Na_2SO_4$ and concentrated in vacuo. 20.2 g of 1-(3,4-dichlorophenyl)-3-(1-t-butoxycarbonyl-4-piperidinyl)-1-cyanopropane are obtained in the form of an oil.

This compound is deprotected by dissolving it in 100 ml of trifluoroacetic acid and by stirring the solution for 30 minutes at room temperature. The acid is concentrated in vacuo, an oil is obtained which is taken up in a 5% sodium hydroxide solution, the mixture is extracted with ether, and the extract is washed successively with water and then with a saturated NaCl solution, dried over $Na_2SO_4$ and concentrated in vacuo. The oil obtained is dissolved in 300 ml of ethyl acetate and then hydrochloric acid is bubbled through the solution until it is colored yellow.

The hydrochloride is separated by filtration.
m=12.4 g
M.p.=182° C.
C) 3-(1-Benzyl-4-piperidinyl)-1-(3,4-dichlorophenyl)-1-cyanopropane.

16.75 g of the amine prepared above according to B) and 15.15 g of triethylamine are dissolved in 150 ml of dichloromethane. 8.98 g of benzyl bromide dissolved in 25 ml of dichloromethane are added dropwise and the mixture is then heated under reflux for one hour. The solvent is concentrated in vacuo and the residue is then taken up in a 5% sodium hydroxide solution. The mixture is extracted with ether and then washed successively with water and with a saturated NaCl solution, dried over $Na_2SO_4$ and concentrated in vacuo.

The oil obtained is dissolved in 150 ml of ethanol, hydrochloric acid is bubbled through and the hydrochloride is filtered.
m=15 g
M.p.=233° C.
D) 4-(1-Benzyl-4-piperidinyl)-2-(3,4-dichlorophenyl)-1-aminobutane.

13.3 g of the product prepared above dissolved in a mixture of 150 ml of ethanol, 20 ml of concentrated ammonia and in the presence of 2 g of Raney nickel are hydrogenated at atmospheric pressure and room temperature. The hydrogenation completed, the reaction mixture is filtered on Celite and the filtrate is concentrated in vacuo after having twice added 100 ml of absolute ethanol.

13.5 g of a colorless oil are obtained.

E) Compound 1

1.95 g of amine prepared above according to D), 0.95 g of 4-fluoronaphthoic acid and 1.01 g of triethylamine are dissolved in 40 ml of dichloromethane. 2.21 g of BOP (N-benzotriazolyloxytrisdimethylaminophosphonium hexafluorophosphate) are added and the reaction mixture is left at room temperature for 24 hours. The solvent is concentrated in vacuo, the residue is taken up in ether and the mixture is washed successively with a 5% sodium hydroxide solution and then with a saturated NaCl solution. The ethereal phase is dried over $Na_2SO_4$ and concentrated in vacuo. The residue is chromatographed on silica gel, eluent: dichloromethane/methanol 93:7 (v/v).

Concentration of the pure fractions yields a residue, starting from which the hydrochloride is prepared in ethyl acetate m=1.31 g M.p.=174°–176° C.

EXAMPLE 2

N-[4-[1-(fluorobenzyl)-4-piperidinyl]-2-(3,4-dichlorophenyl)-butyII-2,4-dichlorobenzamide hydrochloride.

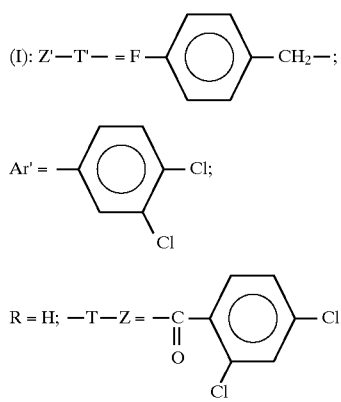

This commound is prepared by route (b) of scheme 2.

A) 1-(3,4-Dichlorophenyl)-3-(1-tert-butoxycarbonyl-4-piperidinyl)-1-cyanopropane.

This compound is prepared according to Example 1 step B but is not deprotected.

B) 2-(3,4-Dichlorophenyl)-4-(1-tert-butoxycarbonyl-4-piperidinyl)-1-aminobutane.

17.4 g of the cyano derivative prepared above are dissolved in 300 ml of ethanol at 95° C., 20 ml of water and 70 ml of concentrated ammonia in the presence of 2 g of Raney Nickel. The mixture is then hydrogenated at room temperature and atmospheric pressure. The hydrogenation completed, the reaction mixture is filtered on Celite and the filtrate is concentrated in vacuo. The residue is taken up in acetone and the precipitate formed is separated by filtration and then dissolved in ether, and washed with a 10% sodium hydroxide solution and then with a saturated NaCl solution. The ethereal phase is dried over $MgSO_4$ and concentrated in vacuo.

m=16.2 g

C) N-[2-(3,4-Dichlorophenyl)-4-(1-tert-butoxycarbonyl-4-piperidinyl)-butyl]-2,4-dichlorobenzamide.

16.2 g of the amide prepared above and 8.16 g of triethylamine are dissolved in 200 ml of dichloromethane. A solution of 9.31 g of 2,4-dichlorobenzoyl chloride is then added dropwise, the reaction mixture is left for three hours at room temperature and then heated to 60° C. for 4 hours, and the solvent is removed in vacuo. The residue is taken up in water and extracted with ethyl acetate. The organic phase is washed successively with a 10% sodium hydroxide solution, twice with water and then with a saturated NaCl solution, dried over $Na_2SO_4$ and concentrated in vacuo. The residue is chromatographed on silica gel, eluent: dichloromethane/methanol 98:2 (v/v). Concentration of the pure fractions yields a residue which is used as such for the deprotection.

D) N-[2-(3,4-Dichlorophenyl)-4-(4-piperidinyl)butyl]-2,4-dichlorobenzamide.

The residue obtained above is taken up in a sodium hydroxide solution and then extracted with dichloromethane. The organic phase is washed with a saturated NaCl solution and then dried over $Na_2SO_4$ and concentrated in vacuo. The residue is crystallised in ethyl acetate.

m=11.6 g

M.p.=118° C.

E) Compound 2

1 g of the compound prepared above and 0.81 g of $K_2CO_3$ are heated to 60° C. in 15 ml of dimethylformamide. 0.37 g of 4-fluorobenzyl bromide is then added and heating is continued at 60° C. with stirring for one hour. The solvent is removed in vacuo, the residue is taken up in water and the mixture is then extracted with ethyl acetate. The organic phase is washed successively with a 10% sodium hydroxide solution, with water and then with a saturated NaCl solution, dried over $MgSO_4$ and concentrated in vacuo.

The residue is chromatographed on silica gel, eluent: dichloromethane/methanol 98:2 (v/v).

Concentration of the pure fractions yields a residue which is taken up in ethyl acetate and from which the hydrochloride is prepared by bubbling through hydrochloric acid.

m=0.6 g

M.p.=110° C.

The compounds described in Tables 1, 2, 3 and 4 which follow are prepared according to the preceding Examples 1 or 2.

TABLE 1

| Example no | Z' | T' | M.p.; °C. | Salt | Route |
|---|---|---|---|---|---|
| 3 | (phenyl) | $-CH_2-$ | 116 | HCl | a |
| 4 | (chlorophenyl) | $-CH_2-$ | 130 | HCl | b |

TABLE 1-continued

Z'—T'—N(piperidine)—(CH₂)₂—CH(3,4-dichlorophenyl)—CH₂—NH—C(=O)—(2,4-dichlorophenyl)

| Example no | Z' | T' | M.p.; °C. | Salt | Route |
|---|---|---|---|---|---|
| 5 | 2,6-dichlorophenyl | —CH₂— | 114 | HCl | b |
| 6 | 4-methoxyphenyl | —CH₂— | 114 | HCl | b |
| 7 | 4-hydroxyphenyl | —CH₂— | 124 | HCl,H₂O | b |
| 8 | 3-pyridyl | —CH₂— | 128 | HCl | b |
| 9 | 4-pyridyl | —CH₂— | 146 | 2HCl, 0,5H₂O | b |
| 10 | 4-cyanophenyl | — | 87 | 0,5H₂O | b |
| 11 | 4-nitrophenyl | — | 82 | base | b |

TABLE 2 phenyl-CH₂—N(piperidine)—(CH₂)₂—CH(3,4-dichlorophenyl)—CH₂—NH—C(=O)—Z

| Example no | Z | M.p.; °C. | Salt | Route |
|---|---|---|---|---|
| 12 | 4-(CH₂N(C₄H₉)₂)phenyl | 146 | 2HCl, 0,8H₂O | a |
| 13 | 2,4-dimethylphenyl | 179 | HCl | a |

TABLE 3

Z'—T'—N(piperidine)—(CH₂)₂—CH(naphthyl)—CH₂—NH—C(=O)—(2,4-dimethoxyphenyl)

| Example no | Z' | T | M.p. °C. | Salt | Route |
|---|---|---|---|---|---|
| 14 | phenyl | —CH₂— | 125 | HCl | a |
| 15 | 2-pyridyl | —C(=O)— | 115 | HCl | a |

TABLE 4

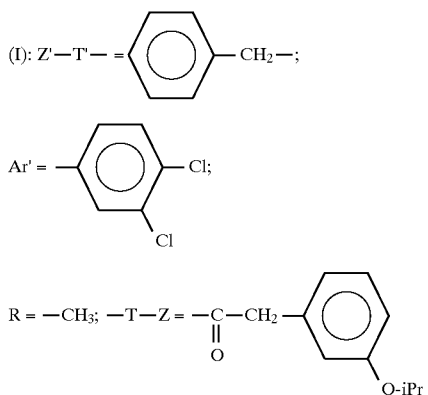

| Example | Z' | M.p.; °C. | Salt | Route |
|---|---|---|---|---|
| 16 | (3-pyridyl) | 105 | HCl | b |
| 17 | (4-pyridyl) | 134 | HCl | b |

EXAMPLE 18

N-Methyl-,N-[4-(1-benzyl-4-piperidinyl)-2-(3,4-dichlorophenyl)-butyl]3-isopropoxyphenylacetamide hydrochloride (I): Z'—T'— = (phenyl)—CH$_2$—;

Ar' = (3,4-dichlorophenyl);

R = —CH$_3$; —T—Z = —C(=O)—CH$_2$—(3-O-iPr-phenyl)

A) Ethyl-N-[4-(1-benzyl-4-piperidinyl)-2-(3,4-dichlorophenyl)-butyl]-carbamate.

2.13 g of the amine prepared according to Example 1, D) are dissolved in 10 ml of dichloromethane and treated at −15° C., under a nitrogen atmosphere, with 0.6 ml of ethyl chloroformate and 1 ml of triethylamine. The reaction mixture is brought back to room temperature, washed successively with 5% NaOH, H$_2$O and saturated NaCl, and dried over MgSO$_4$. 2.25 g of colorless oil are obtained.

B) N-methyl-4-(1-Benzyl-4-piperidinyl)-2-(3,4-dichlorophenyl)-butylamine hydrochloride.

The carbamate obtained above is dissolved in 20 ml of THF. The mixture is added to 0.50 g of LiAlH$_4$ suspended in 20 ml of THF. The mixture is allowed to react for 3 hours under reflux, 2.5 ml of H$_2$O are then added at 0° C., the mixture is filtered and the filtrate is evaporated. The oil is redissolved in dichloromethane and the hydrochloride is precipitated by adding a solution of HCl/4N ether.

m=2.45 g

M.p.=185° C.

C) Compound 18

1 g of the diamine prepared above is dissolved in 15 ml of CH$_2$Cl$_2$. 1 ml of triethylamine, 400 ml of 3-isopropoxyphenylacetic acid and 1.06 g of BOP (N-benzothiazolyloxytrisdimethylaminophosphonium hexafluorophosphate) are added successively and the mixture is left at room temperature for 30 minutes. The solvent is evaporated in vacuo, the residue is taken up in ethyl acetate, and the mixture is washed successively with 5% NaOH and a solution of water saturated with NaCl, dried over MgSO$_4$ and evaporated. The residue is chromatographed on silica gel, eluent: CH$_2$Cl$_2$/CH$_3$OH 98:2 (v/v). Concentration of the pure fractions yields a residue, starting from which the hydrochloride is prepared in dichloromethane.

m=0.60 g

M.p.=106° C.

Proceeding according to Example 18 above, the compounds 19 to 22 described in Table 5 below are prepared.

TABLE 5

| Example no | Z' | T' | M.p.; °C. | Salt | Z | Route |
|---|---|---|---|---|---|---|
| 19 | phenyl | —CH$_2$— | 110 | HCl | 2,5-dimethoxybenzyl (—CH$_2$—C$_6$H$_3$(OCH$_3$)$_2$) | b |
| 20 | phenyl | —CH$_2$— | 119 | HCl | 2-(1-methoxyethyl)benzyl | b |
| 21 | 2-pyridyl | —C(O)— | 90 | HCl | 2,5-dimethoxybenzyl | b |
| 22 | phenyl | —CH$_2$— | 105 | HCl | (S)—CH(OH)—phenyl | b |

EXAMPLE 23

N-Methyl-N-[4-[1-(4-methoxybenzyl)-4-piperidinyl]-2-(3,4-dichlorophenyl)-butyl]-3-chlorophenylacetamide hydrochloride.

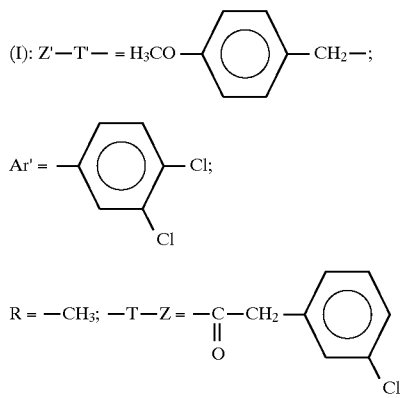

(I): Z'—T'— = H$_3$CO—C$_6$H$_4$—CH$_2$—;

Ar' = 3,4-dichlorophenyl;

R = —CH$_3$; —T—Z = —C(O)—CH$_2$—(3-chlorophenyl)

This compound is prepared according to route b of scheme 2.

A) 1-(3,4-Dichlorophenyl)-3-(1-trityl-4-piperidinyl)-1-cyanopropane.

25 g of 1-(3,4-dichlorophenyl)-3-(4-piperidinyl)-1-cyanopropane hydrochloride (Example 1B) are dissolved in 400 ml of CH$_2$Cl$_2$. 22 g of trityl chloride and 21 ml of triethylamine are added dropwise to the solution. The reaction mixture is left for 2 hours without stirring, and washed successively with H$_2$O, an aqueous solution buffered to pH=2, and a solution saturated with NaCl. It is dried over MgSO$_4$ and evaporated. The residue is chromatographed on silica gel, eluent: heptanel ethyl acetate 9:1 (v/v). 39 g of oil are obtained.

B) 2-(3,4-Dichlorophenyl)-4-(1-trityl-4-piperidinyl)-1-butaneamine.

The oil prepared above is dissolved in 500 ml of glycol monomethyl ether; 50 ml of ammonia are added and a hydrogenation under atmospheric pressure and at room temperature is carried out in the presence of Raney Ni. The mixture is carried then evaporated in vacuo and 39 g of oil are obtained.

C) N-methyl-2-(3,4-Dichlorophenyl)-4-(1-trityl-4-piperidinyl)-butylamine.

The oil prepared above is dissolved in 250 ml ot dichloromethane at −15° C. under nitrogen and treated with 8 g of ethyl chloroformate and 10 ml of triethylamine. After washing with 5% NaOH, H$_2$O and a saturated NaCl solution, the organic phase is dried and evaporated. The oil obtained is taken up in 200 ml of THF and poured dropwise onto 5.2 g of LiAlH$_4$ suspended in 200 ml of THF. After refluxing for 3 hours, the reaction mixture is cooled and 27 ml of H$_2$O are added. The mixture is filtered, the filtrate is evaporated and the residue is chromatographed on silica gel, eluent: CH$_2$Cl$_2$/MeOH 100:2 (v/v). 24 g of oil are obtained.

D) N-methyl-N-[4-[1-trityl-4-piperidinyl]-2-(3,4-dichlorophenyl)-butyl]-3-chlorophenylacetamide.

11.53 g of the above amine, 3.8 g of 3-chlorophenylacetic acid, 3 ml of triethylamine and 9.73 g of BOP are dissolved successively in 200 ml of $CH_2Cl_2$. After reacting for 30 minutes, the mixture is washed with a 5% NaOH solution and $H_2O$, dried over $MgSO_4$ and evaporated. The residue is chromatographed on silica gel, eluent: pentane/ethyl acetate 80:20 (v/v). The fractions are concentrated to obtain 8 g of a foam.

E) Compound 23

8.0 g of the amine obtained above are dissolved in 50 ml of formic acid; 50 ml of $H_2O$ are added dropwise. The mixture is allowed to react for 30 minutes at 60° C., filtered and evaporated, and the residue is taken up in 100 ml of $H_2O$, the mixture is rendered basic with a 30% NaOH solution to pH 10 and extracted twice with 150 ml portions of ethyl ether, dried over $MgSO_4$ and evaporated. 6 g of oil are obtained, of which 2.2 g are taken to dissolve them in 15 ml of DMF. 5 g of $K_2CO_3$ and 0.75 g of paramethoxybenzyl chloride are added. The mixture is allowed to react at 65° C. for 2 hours and the reaction mixture is then poured into 250 ml of $H_2O$. The mixture is extracted twice with 200 ml portions of ether, and the organic phase is washed with $H_2O$, dried over $MgSO_4$, filtered and evaporated. The residue is purified by chromatography on silica gel, eluent: $CH_2Cl_2$/$CH_3OH$ 98:2 (v/v). Concentration of the pure fractions yields a residue starting from which the hydrochloride is prepared in dichloromethane.

m=2 g

M.p.=100° C.

Proceeding according to Example 23, the compounds described in Table 6 below are prepared.

TABLE 6

| Example no | Z' | Z | M.p.; °C. | Salt | Route |
|---|---|---|---|---|---|
| 24 | 4-hydroxyphenyl | 2-chlorophenyl | 124 | HCl | b |
| 25 | 4-hydroxyphenyl | 2-fluoro-?-fluorophenyl | 120 | HCl | b |

EXAMPLE 26

N-Methyl-N-[4-(1-hydroxybenzyl-4-piperidinyl)-2-(3,4-dichlorophenyl)-butyl]-3-isopropoxyphenylacetamide hydrochloride.

(I): Z'—T' = HO 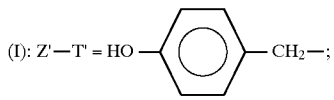 —CH$_2$—;

Ar' = 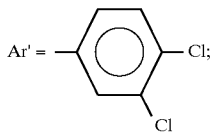 —Cl;

R = —CH$_3$; —T—Z = —C—CH$_2$— 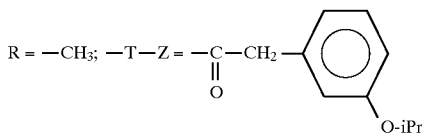
  ‖
  O

A) Methyl-4-(methoxymethyl ether) benzoate.

The reaction is carried out according to: Synthesis 1976, 244.

15.3 g of methylparaben (methyl-4-hydroxy benzoate) are dissolved in 500 ml of dichloromethane. 50 ml of dimethoxymethane and a spatula tip full of paratoluenesulphonic acid are added. The mixture is left under reflux over a Soxhlet provided with 3 Angstrom molecular sieve. After reacting for 24 hours, the product is filtered, washed successively with a solution of $NaHCO_3$, with water and with a saturated NaCl solution and then the organic phase is evaporated. 17 g of yellow liquid are obtained.

B) 4-(Methoxymethyl ether)benzyl alcohol.

17 g of the product prepared above diluted in 100 ml of THF are added to 5 g of $LiAlH_4$ suspended in 75 ml of THF. The mixture is evaporated and the residue is chromatographed on silica gel, eluent: heptane/ethyl acetate 8:2 (v/v). 15 g of colorless oil are obtained.

C) 4-(Methoxymethyl)benzyl ether chloride.

10 g of the oil above are dissolved in 20 ml of acetonitrile and then 15 g of triphenylphosphine and 8 g of N-chlorosuccinimide are added at 0° C. After 1 hour, the mixture is evaporated, the residue is taken up in ether, the mixture is filtered and the filtrate is evaporated. The residue is chromatographed on silica gel, eluent: heptane/ethyl acetate 9:1 (v/v). 4.3 g of expected product are obtained.

D) N-methyl-N-[4-(1-trityl-4-piperidinyl)-2-(3,4-dichlorophenyl)-butyl]-3-isopropoxyphenylacetamide.

3 g of the amine prepared according to Example 23 step C, 1.05 g of 3-isopropoxyphenylacetic acid, 0.70 g of triethylamine and 2.4 g of BOP are dissolved in 50 ml of $CH_2Cl_2$. After reacting for 30 minutes, the mixture is washed with a 5% NaOH solution, with water and then with a saturated NaCl solution. It is dried over $MgSO_4$ and evaporated. 3.8 g of oil are obtained.

E) N-methyl-N-[4-tl-(methoxymethyl)benzylether-4-piperidinyl]-2-(3,4-dichlorophenyl)-butyl]-3-isopropoxyphenylacetamide.

The oil obtained above is dissolved in 35 ml of formic acid; 25 ml of $H_2O$ are added to the solution and it is allowed to react for 30 minutes at 60° C. The mixture is filtered, the filtrate is evaporated and the oil obtained is redissolved in 50 ml of $H_2O$. The solution is rendered basic to pH 10, extracted with ether and dried over $MgSO_4$. 2.8 g of oil are obtained after evaporation, which are dissolved in 20 ml of DMF. 5 g of $K_2CO_3$ and 1.2 g of 4-(methoxymethyl)benzyl ether chloride (prepared in C) are added. After reacting for 2 hours at 65° C., the mixture is poured into 200 ml of H₂O and extracted with ether, and the extract is washed with H₂O, dried over MgSO₄ and evaporated. 3.5 g of oil are obtained.

F) Compound 26

The oil obtained above is diluted in 25 ml of THF, 25 ml of 2-propanol and 15 ml of HCl/ether solution (4N). After stirring for 2 hours, the mixture is evaporated and chromatographed on silica gel, eluent: CH₂Cl₂/CH₃OH 98:2 (v/v).

m=2.5 g

M.p.=125° C.

EXAMPLE 27

N-benzyl-1-methyl-4-(3-(3,4-dichlorophenyl)-4-[N'-methyl-(3-isopropoxy) acetamido]-butyl)-piperidinium iodide.

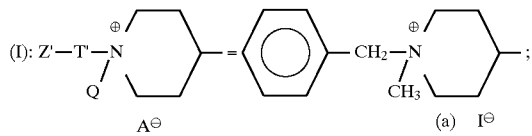

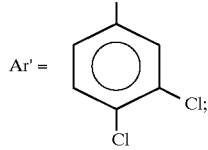

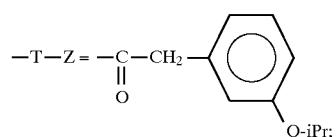

1.5 g of the compound prepared according to Example 18 are dissolved in 50 ml of CH₂Cl₂. The mixture is stirred with 10 ml of a 10% NaOH solution, and the organic phase is dried over MgSO₄ and evaporated. The oil obtained is dissolved in 50 ml of methyl iodide, left for one hour at room temperature and then evaporated. The residue is chromatographed on silica gel H, eluent: CH₂Cl₂/CH₃OH 97:3 (v/v). The fractions of pure product are concentrated.

m=1.3 g

M.p.=108° C.

The methyl group in position 1 on the piperidine is of axial configuration.

¹³C NMR spectrum:

N—CH₃ axial: δ=44.18 ppm

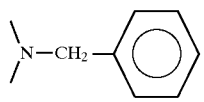

equatorial: δ=69.76 ppm

EXAMPLE 28

N-benzyl-1-methyl-4-(3-(3,4-dichlorophenyl)-4-[N'-methyl-(3-isopropoxy) acetamido]-butyl)-piperidinium iodide.

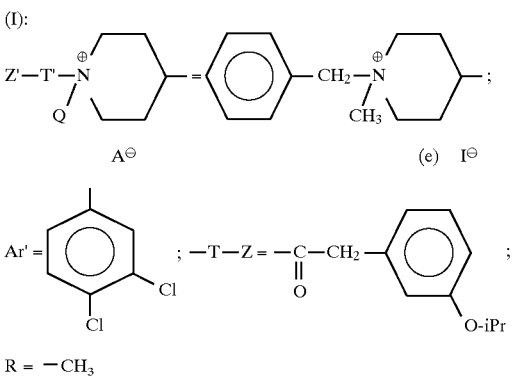

The above chromatography column is eluted with a CH₂Cl₂/CH₃OH 95:5 (v/v) mixture to obtain 0.20 g of a fraction corresponding to the product in which the methyl in position 1 of the piperidine is of equatorial configuration.

M.p.=105° C.

¹³C NMR spectrum:

N—CH₃ equatorial: δ=51.20 ppm

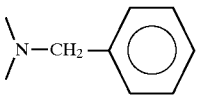

axial: δ=59.85 ppm

We claim:

1. A compound of formula XXII:

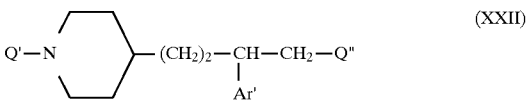

in which

Ar' represents a phenyl, unsubstituted or substituted one or more times with a halogen atom, C₁–C₃ alkyl, trifluoromethyl, C₁–C₃ alkoxy, or hydroxyl; a thienyl, pyridyl or naphthyl group, the said groups being unsubstituted or substituted with a halogen atom; an indolyl group or a benzothienyl group;

either Q' is hydrogen or an N-protecting group selected from the group consisting of formyl, acetyl, propionyl, t-butoxycarbonyl, methoxypropionyl, trichloroethoxycarbonyl, monochloromethylcarbonyl, monochloroethylcarbonyl, dichloroethylcarbonyl, trichloromethylcarbonyl, trichloropropylcarbonyl, benzyloxycarbonyl, 4-nitrobenzyloxycarbonyl, benzoyl, 2,4-dichlorobenzoyl, 4-fluoro-1-naphthylcarbonyl, benzyl, diphenylmethylbis(4-methoxyphenyl)methyl, triphenylmethyl, (4-methoxyphenyl)-diphenylmethyl, and bis(4-methoxyphenyl) phenylmethyl, and Q" is an amino group or a group:

or Q' is a group:

and Q" is an amino group,

R represents hydrogen, a methyl group or a group $(CH_2\text{—})_n\text{—L}$, where n is an integer from 2 to 6 and L is hydrogen or an amino group, Z and Z' represent, independently, a hydrogen atom or a group M or OM, M represents linear or branched $C_1$–$C_6$ alkyl; α-hydroxybenzyl, α-alkylbenzyl or phenylalkyl in which the alkyl group contains 1 to 3 carbon atoms, and which is unsubstituted, mono- or polysubstituted on the aromatic ring with halogen, hydroxyl, alkoxy of 1 to 4 carbon atoms, alkyl of 1 to 4 carbon atoms; pyridylalkyl in which the alkyl group contains 1 to 3 carbon atoms; naphthylalkyl in which the alkyl group contains 1 to 3 carbon atoms; pyridylthioalkyl in which the alkyl group contains 1 to 3 carbon atoms; styryl; 1-methyl-2-imidazolythioalkyl in which the alkyl group contains 1 to 3 carbon atoms; 1-oxophenyl-3-indan-2-yl;or an aromatic or heteroaromatic group selected from the group consisting of Phenyl which is unsubstituted or mono- or polysubstituted by halogen, $C_1$–$C_4$-alkyl, $C_1$–$C_4$-alkoxy, CN, $NO_2$, $CF_3$, or hydroxyl; naphthyl, said naphthyl being unsubstituted or mono- or polysubstituted by halogen, $C_1$–$C_4$-alkyl or hydroxyl; pyridyl, thienyl, indoyl and benzothienyl, said pyridyl, thienyl, indoyl and benzothienyl group being unsubstituted or mono- or polysubstituted by $C_1$–$C_4$-alkyl or hydroxyl, T represents a group selected from

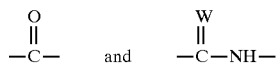

W being an oxygen or sulphur atom, with the limitation that when Z' is hydrogen or OM, T' is other than a bond; and when Z is hydrogen or OM, T is other than a group —C(W)—NH—, T' represents a bond, a —$CH_2$— group or a —C(O)— group, provided that when Q" is —N(R)—T—Z, Q' is different from formyl, acetyl, propionyl, t-butoxycarbonyl, benzyloxycarbonyl, benzoyl 2,4-dichlorobenzoyl, 4-fluoro-1-naphthylcarbonyl, and benzyl, or an acid addition salt thereof.

2. The compound of claim 1, wherein said halogen is chlorine or fluorine.

* * * * *